United States Patent

Craig et al.

Patent Number: 5,958,201
Date of Patent: *Sep. 28, 1999

[54] SODIUM ION-SELECTIVE-ELECTRODE MEMBRANE HAVING EXTENDED USELIFE

[75] Inventors: Alan Robert Craig; Michael Patrick Reidy, both of Wilmington, Del.

[73] Assignee: Dade Behring Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/703,121

[22] Filed: Aug. 26, 1996

[51] Int. Cl.$^6$ .................................................. G01N 27/333
[52] U.S. Cl. ......................... 204/418; 204/416; 205/789.5
[58] Field of Search ................................. 204/416, 418, 204/419; 205/789, 789.5

[56] References Cited

U.S. PATENT DOCUMENTS

| | | | |
|---|---|---|---|
| 4,214,968 | 7/1980 | Battaglia et al. | 204/418 |
| 4,454,007 | 6/1984 | Pace | 204/403 |
| 4,505,800 | 3/1985 | Toner et al. | 204/418 |
| 4,571,293 | 2/1986 | Seshimoto et al. | 204/418 |
| 4,578,173 | 3/1986 | Seshimoto et al. | 204/416 |
| 4,608,149 | 8/1986 | Daniel et al. | 204/418 |
| 4,615,788 | 10/1986 | Seshimoto et al. | 204/418 |
| 4,735,702 | 4/1988 | Reinhoudt et al. | 204/418 |
| 4,882,292 | 11/1989 | Sudholter et al. | 204/418 |
| 5,035,791 | 7/1991 | Battilotti et al. | 204/418 |
| 5,284,568 | 2/1994 | Pace et al. | 204/403 |
| 5,401,377 | 3/1995 | Shieh et al. | 204/418 |
| 5,413,685 | 5/1995 | Ozawa et al. | 204/418 |
| 5,522,978 | 6/1996 | Pace et al. | 204/418 |

FOREIGN PATENT DOCUMENTS

| | | |
|---|---|---|
| 0 221 508 A1 | 5/1987 | European Pat. Off. . |
| 0 230 573 A1 | 8/1987 | European Pat. Off. . |
| 0221508 B1 | 1/1994 | European Pat. Off. . |

OTHER PUBLICATIONS

Study of the Behaviour of Calix[4]arene–Based Sodium–Selective Electrodes by Means of ANOVA; *Analytical Chemistry*; vol. 65 No. 21; pp. 3156–3160; Nov. 1993.

*Primary Examiner*—T. Tung
*Attorney, Agent, or Firm*—Leland K Jordan

[57] ABSTRACT

A method for extending the uselife of a sodium ion selective membrane of an ISE sensor by incorporating water therein. Also provided are polymer compositions comprised of water plus the membrane compounds or residues and articles comprising such compositions.

4 Claims, 3 Drawing Sheets

SODIUM ION-SELECTIVE-ELECTRODE MEMBRANE HAVING EXTENDED USELIFE

BACKGROUND OF THE INVENTION

1. Field of the Invention

This invention relates generally to ion sensors, and more particularly relates to ion-selective-electrode sensors and for methods for production of sensors having extended useful life.

2. Description of the Related Art

Ion-selective-electrode (ISE) sensors that can measure the activity or concentration of analyte ions and metabolites are useful in the analysis of biological fluids including blood, urine, plasma, saliva, spinal fluid, and serum. Such fluids, particularly urine samples, often contain various substances such as drugs and ionic species which can interfere with the determination of the ions to be determined. A primary requirement of the sensor is that it have a high sensitivity to the analyte of interest so that it can accurately determine the concentration of that analyte. Another important requirement is that the sensor has minimal response to ionic species other than the analyte of interest, a characteristic known as selectivity. For example, ISE sensors that are used to determine sodium ions must have a high sensitivity to sodium and also must have a high selectivity for sodium so that the sensor's signals are not affected by the presence of related ions like potassium or chloride.

Recently, solid state ISE sensors have been developed that have cost and convenience in use advantages over conventional ISE sensors as there is no liquid electrolyte solution interposed between a reference electrode and a sensing electrode used to measure the activity of various analyte ions and metabolites. Solid state sensors use a polymeric membrane incorporating an ion-selective agent or ionophore to complex or otherwise attach to the desired ion and, ideally attach only to the desired ion, to provide the sensor's sensitivity and selectivity. The membrane further includes a solvent for the ionophore so that the complexed ion is mobile within the membrane. The membrane thereby changes its ionic content in response to contact with an ionic species analyte in a fluid. In some sensors, multiple analytes may be measured by providing a common fluid flow in contact with different membranes designed for sensitivity to different analytes. In this mode of use, fluids being analyzed are caused to directly contact the membrane layer repeatedly requiring that the membrane's sensitivity and selectivity in combination with the electrode remain constant during repeated exposure to fluids. Stability of the sensors's selectivity is critical, as failure to maintain constant selectivity during repeated exposure to fluids may result in inaccurate readings or spurious signals. Changes in specificity will adversely limit the uselife of the sensor. Thus a factor limiting the uselife of an ISE sensor is the retention of, or stability of, the membrane's selectivity for the analyte of interest compared to other related substances during repeated exposure of the membrane to a variety of fluids. For example, membranes designed to measure sodium need to have a known response to other ionic species that may be included in calibrator fluids (e.g. calcium or potassium ions). Uselife is defined as the number of hours a sensor may be exposed to a standard test fluid without causing the calibration slope after exposure to deviate from the calibration slope before exposure by more than 10%.

There is general theoretical understanding of the requirements for producing sensitivity and selectivity within an ISE sensor membrane, however, theory has poor predictive value for defining the chemical structure of a membrane required to retain stability of the critical sensitivity and selectivity characteristics during actual use. This situation is exacerbated since any additives incorporated into the membrane to enhance its stability must be carefully chosen so as to not interfere with the polymeric binder, ionophore, solvent and other chemicals that may be included for plasticizing, manufacturability, etc.

It is known to use a certain class of solvents with potassium ISE sensor membrane compositions containing valinomycin to extend its shelf life (U.S. Pat No. 4, 608, 149). In this case, a hydrophobic polymer is used as the binder and the selected solvents plasticize the membrane while being substantially nonvolatile. The nonvolatile nature of the solvent provides extended shelf life for the membrane before operation of the sensor. However this does not address extending the uselife of the sensor.

A remaining shortcoming in sodium ISE sensors is the degradation in the membrane's selectivity as a result of repeated exposure to test fluids containing the analyte of interest as well as substances in the sample fluids other than the analyte of interest Thus, there is a need for a simple and inexpensive method to extend the uselife of ISE sensors by lengthening the stability of the membrane's selectivity characteristics.

SUMMARY OF THE INVENTION

The present invention addresses the problem of extending the useful selectivity of sodium ISE sensors by incorporating a predetermined amount of water into the sodium membrane paste during manufacture. The extended uselife is quite unexpected since the selectivity of the sensor is primarily determined by the chemical constituents of the membrane and the ionophores generally used in sodium ISE membranes are not highly hydrophilic. In addition to the ionophore, the membrane paste comprises a water insoluble organic solvent, a hydrophobic organic polymer, and other ingredients like silica, a plasticizer, and an adhesion promoter, none of which are expected to react favorably with water to extend membrane stability in use. Thus the stability of selectivity of the membrane is not expected to be affected by the inclusion of water into the membrane paste used in production. It has however been determined that an ISE sensor having a membrane produced from a polymeric matrix paste with between about 0.50 percent by weight and 1.00 percent by weight of water has a uselife that is as much as twice as long as a membrane produced from a polymeric matrix paste not having added water.

A further advantage of the present invention is that the incorporation of water into the membrane during manufacture is simple and does not require expensive ingredients or chemically complex procedures.

DETAILED DESCRIPTION OF THE INVENTION

Figure 1A:
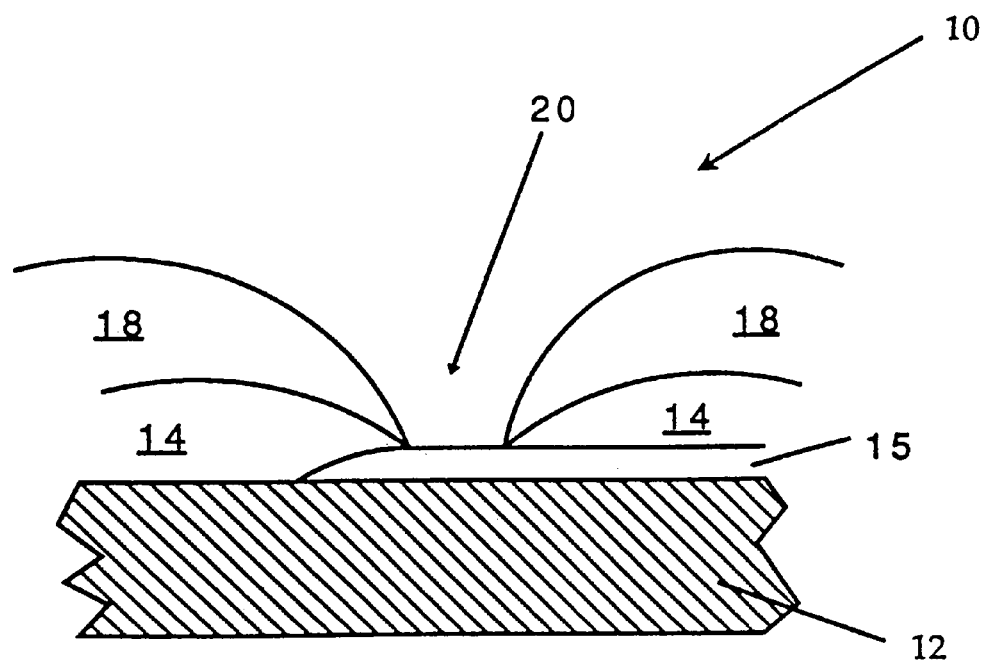
FIGS. 1a and 1b are partial sectional views of a sensor illustrating the location of a membrane exemplary of the present invention.
Figure 1B:
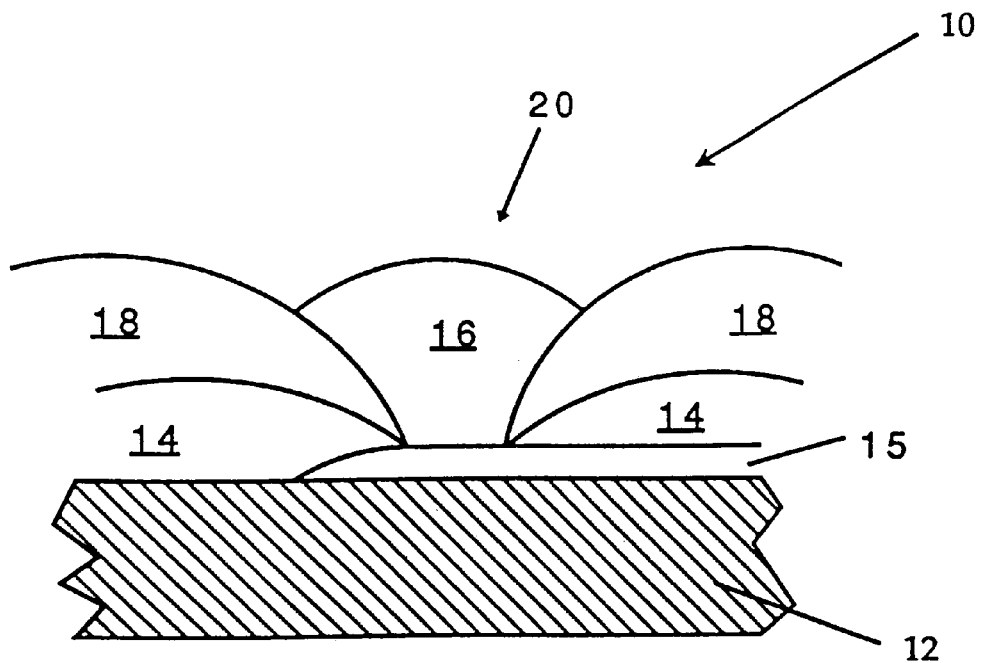

FIG. 1a shows a partially complete ISE sensor 10 comprising a first dielectric layer 14 and a second dielectric layer 18 formed on a sensor base 12 in contact with a conductive electrode path 15, the layers 14 and 18 having patterns of openings, the openings aligned to form a cavity, generally indicated by the numeral 20. FIG. 1b further shows a sensor membrane 16 applied within the cavity 20 in contact with the conductive path 15. The process for making such a sensor, preferably using conventional thick film screen printing techniques and suitable drying means, is well known in the art, for example, as described in U.S. Pat. No. 4,454,007, assigned to the assignee of the present invention. The purpose of the dielectric layers 14 and 18 is to provide sufficient depth to cavity 20, generally between 20 and 40 microns, to accommodate the required thickness of sensor membrane layer 16. An interfacial layer composed of a conductive metal and conductive metal-salt compounds may optionally be disposed between the conductor layer 15 and the sensor membrane layer 16 to stabilize that interface.

The sensors 10 of the present invention are useful for the potentiometric determination of sodium ions in biological test fluids including blood, urine, plasma, saliva, spinal fluid, and serum. Such fluids, particularly urine samples, often contain various substances such as drugs and basic cations which can interfere with the determination of the ions to be determined. A primary requirement of the membrane layer 16 is that it retain its selectivity and its sensitivity to the analyte ion of interest during repeated exposures to test fluids having related ionic species like potassium and chloride.

A variety of ion selective membrane paste compositions may be used for the membrane layer 16, generally comprising an ion-selective agent or ionophore for a sodium ion of interest to provide the desired selectivity and sensitivity, a solvent capable of dissolving the ionophore and a supporting matrix comprised of water plus one or more binder materials. The binder matrix can be any material which is capable of forming a film of sufficient permeability to produce, in combination with the ionophore and solvent, analyte ion mobility across the film as well as retain membrane integrity during repeated exposures to test fluids. The solvent used can be any solvent commonly used to prepare conventional membranes. Optionally, a suitable amount of plasticizer, as well as other components, such as fumed silica and silanes may be included in the membrane. The plasticizer, if included, can be added to the polymer along with the ionophore. U.S. Pat. No. 5,401,377 contains information about the various chemical constituents and applicable production processes useful in production of ISE sensors having an ion-sensitive member in direct contact with an electrical conductor and is generally indicative of the state-of-the art.

A silane coupling agent may be added to the membrane paste to improve the adhesion of membrane layer 16 to the dielectric layers 14 and 18 used to form the surrounding cavity 20, and to the base 12 and conductive paths 15. Useful silanes include bi-functional silanes having an epoxy and a silanoxy moiety. It has been observed that adhesion failures between these three layers result in flaking of the membrane 16 away from the dielectric layers 14 and 18. Such flaking allows test fluids to directly contact the conductive path 15 and cause premature failure of the sensor 10. Silane coupling chemistry is known to be affected by moisture since silane coupling to a surface requires some amount of water to prehydrolyze the silanoxy groups to form silanols. Regardless, it is not fully understood why the presence of water extends the uselife of the membranes used in the Examples, especially since the water is present in an amount that might be expected to fully hydrolyze the reactive silane cations that normally provide an adhering action between the membrane layer 16 and the dielectric layers 14 and 18, the base 12 or conductive paths 15 and render the silane inoperative. It was thus unexpected that the addition of water to the membrane paste could improve the uselife of ISE sensors. However, studies confirmed that the addition of between about 0.50 percent by weight and 1.00 percent by weight water to the membrane paste composition increased the uselife of sodium ISE sensors at least twice as long as membrane compositions without added water.

Notwithstanding the performance sensitivity of sodium membrane 16 to its chemical constituents, it has been discovered that water may be advantageously incorporated into the paste used to produce membrane 16 to increase the membrane's retention or stability of ionic sensitivity and selectivity during repeated exposure to test fluids and to thereby extend the uselife of sodium ISE sensors. Uselife is defined as the number of hours a sensor may be exposed to a standard test fluid comprising a standard aqueous solution of sodium and potassium chloride and carbonate having a pH in the range about 9.0 to 9.5 and an ionic strength of approximately 150 millimolar without causing the calibration slope after exposure to deviate from the calibration slope before exposure by more than 10%.

The water is at a concentration of between about 0.50 percent by weight and 1.00 percent by weight in a membrane paste made of various constituents each having functions that are not generally expected to be enhanced by the deliberate addition of water in an excess amount. Although subject to much speculation, it is thus not fully understood why the presence of water provides an unexpected improvement to the stability of the membranes used in the Examples hereinbelow. Sensor membranes exemplary of this invention are designed to give accurate sodium test results for an average minimum of 48 hours, and as long as 72 hours of use compared to an average 24 hour uselife of previous membranes.

Surprisingly, in view of these results, concurrent studies showed that membrane paste compositions for producing potassium and chloride sensitive membranes in ISE sensors also having between about 0.50 percent by weight and 1.00 percent by weight incorporated therein produced membranes that performed at least as well up to 72 hours as potassium and chloride sensitive membranes produced using paste compositions without added water.

Useful membranes including hydrophobic binder materials, an ionophore, and solvents are prepared using known film-coating or casting or screen printing techniques. Materials including synthetic and natural polymeric materials, such as poly(vinyl chloride), carboxylated poly(vinyl chloride), poly(styrene-co-styrene sulfonic acid), poly(vinyl chloride-co-styrene sulfonic acid), poly(vinyl chloride-co-styrene carboxylic acid) and the like may be used to advantage. High molecular weight poly(vinyl chloride) has been successfully used in the practice of this invention. Useful plasticizers include 2-ethyl hexyl adipate and/or dioctyl sebacate.

Useful "sodium ion-selective agents or ionophores" include any substance which provides for selective interaction with sodium. Examples of sodium-ionophores include naturally occurring monensin, monensin ester derivatives such as methyl, ethyl, butyl, and dodecyl ester monensins, polyether diamide, biscrown ether, cryptand, calixarene, hemispherand, 16-crown-5 derivatives, and Fluka III (4-octadecanoylocymethyl)-N,N,N',N'-tetracylcohexyl-1,2-phenylenedioxydiacetamide). All of these ionophores may be obtained from commercial sources, such as Fluka Chemika-BioChemika (Ronkonkoma, N.Y.), and others known within the industry.

Useful "potassium ion-selective agents or ionophores" include any substance which provides for selective interaction with potassium. Valinomycin is a particularly useful potassium ionophore. Useful "chloride ion-selective agents or ionophores" include any substance which provides for selective interaction with chloride. TDMAC (tridodecylmethylamonium chloride) is a particularly useful chloride ionophore.

The ionophore is dissolved by one or more organic solvents thereby providing analyte ion mobility within the membrane. Useful solvents include phthalates, sebacates, aromatic and aliphatic ethers, phosphates, mixed aromatic aliphatic phosphonates, adipates, nitrated ethers or esters or mixtures thereof, and others known in the art. Particularly useful solvents include 2-ethyl hexyl adipate and dioctyl sebacate.

A volatile solvent may also used to aid manufacturing of the membrane. Such a solvent lowers the viscosity of the membrane composition to facilitate application of the membrane to the sensor. The solvent is removed in the curing step described below. Useful solvents for this purpose include known solvents for the polymeric binders described above. In the case of carboxylated PVC, isophorone is a preferred solvent. Cydohexanone, dimethylformamide, or other highly polar sovents may also be used.

The water used in the present invention was purified by deionization to an electrical resistivity of 10-6 Sieman.

Any order of mixing for the polymer, ionophore, water and plasticizer can be used in preparing the ISE sensor membrane paste exemplary of this invention. Preferably, the analyte-ionophore and plasticizer are added to a mixture of the polymer, fumed silica, water, and volatile solvent. Then silane, if included, is added and mixed to uniformity with shaking. The resulting analyte-selective membrane paste composition can then be used to prepare ISE membranes 16 which, in turn, can be used to prepare ISE sensors 10.

The sensor design, the substrate and the polymeric paste used to prepare the undried membranes were prepared according to the process described in U.S. Pat. No. 5,522,978 assigned to the assignee of the present invention and hereby incorporated by reference. By way of example, one first deposits the conductor paths 15 on the sensor base 12, typically using a conventional silver conductor paste, for instance series QS175, available from E. I. du Pont de Nemours & Co., Wilmington, Delaware, then the first dielectric layer 14, typically a conventional ceramic dielectric paste, for instance series QS482, the second dielectric layer 18 also for instance series QS482, and finally the sensor membrane layer 16. Acceptable materials for the sensor bases 12 are alumina, glass, glass-epoxy composites, polyester, polyethylene, polyimides, polystyrene or polycarbonate. A sodium-selective sensor paste containing, for example, the ingredients described in Table 1 may be dispensed using a syringe onto the electrical conductor 15 at the sodium-selective ISE sensor location 10-Na to form the sodium-selective membrane of the sodium-ISE sensor depicted in FIGS. 1 and 2. Similarly, potassium-selective and chloride-selective sensor pastes also comprising the ingredients described in Table 1 may be dispensed using a syringe onto electrical conductors 15 at the respective potassium and chloride-selective ISE sensor locations 10-K and 10-Cl to form the ion-selective membrane of the potassium and chloride ISE sensors also depicted in FIGS. 1 and 2.

Figure 3:
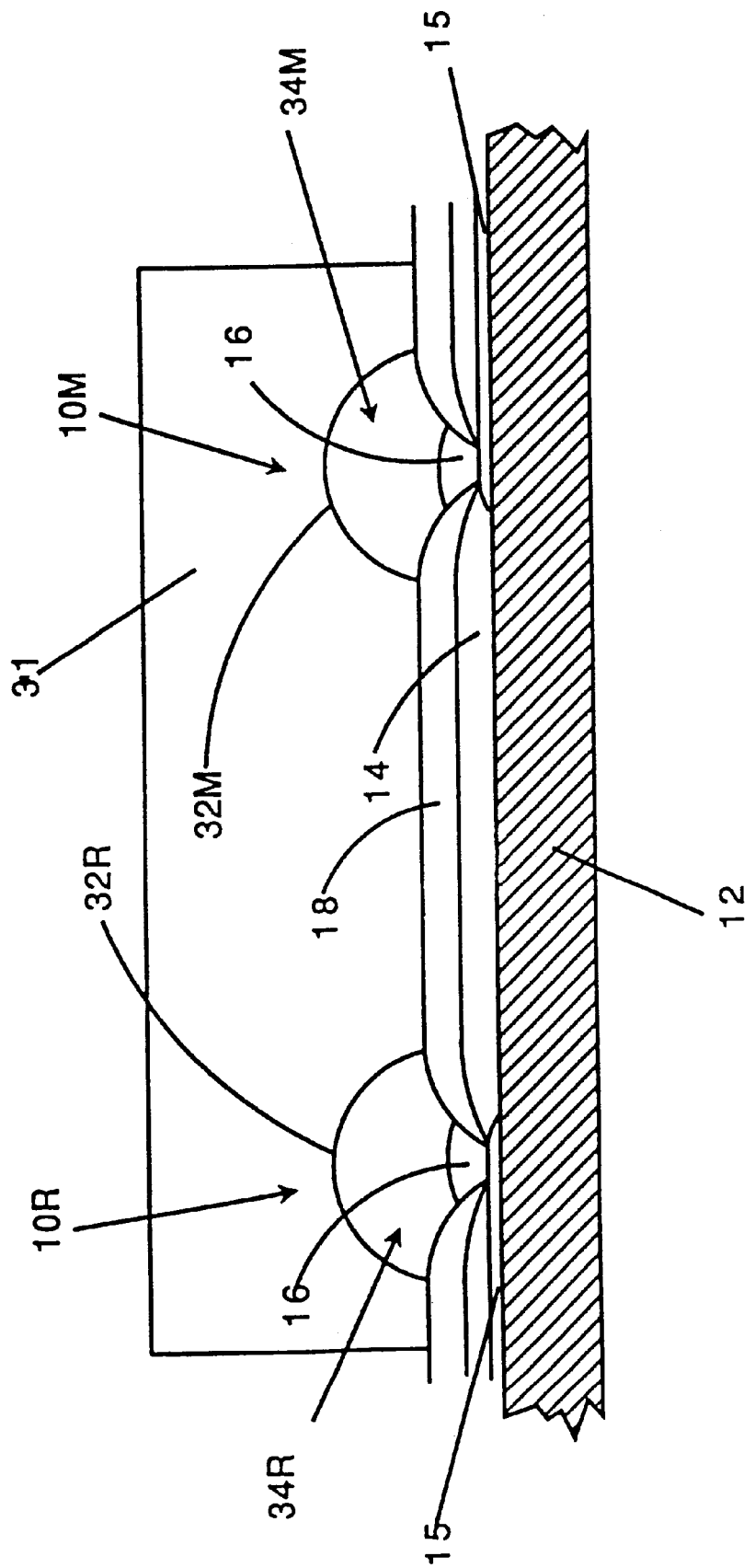

The membrane paste compositions may be cured, thereby removing water from the polymeric paste by heating at a temperature in the range 80° to 110° C. for between 10 and 90 minutes to form ion-selective membrane layer 16. The resulting sensors 10 are then positioned against a flow channel member 31 (FIG. 3). The flow channel member 31 is mounted within an assembly cartridge (not shown) under compression against the base 12 to effect a fluid seal along reference and form sample flow channels 34R and 34M for reference and sample liquids that flow over the ISE sensors 10 where 10R indicates a reference ISE sensor and 10M indicates a measuring ISE sensor.

Figure 2:
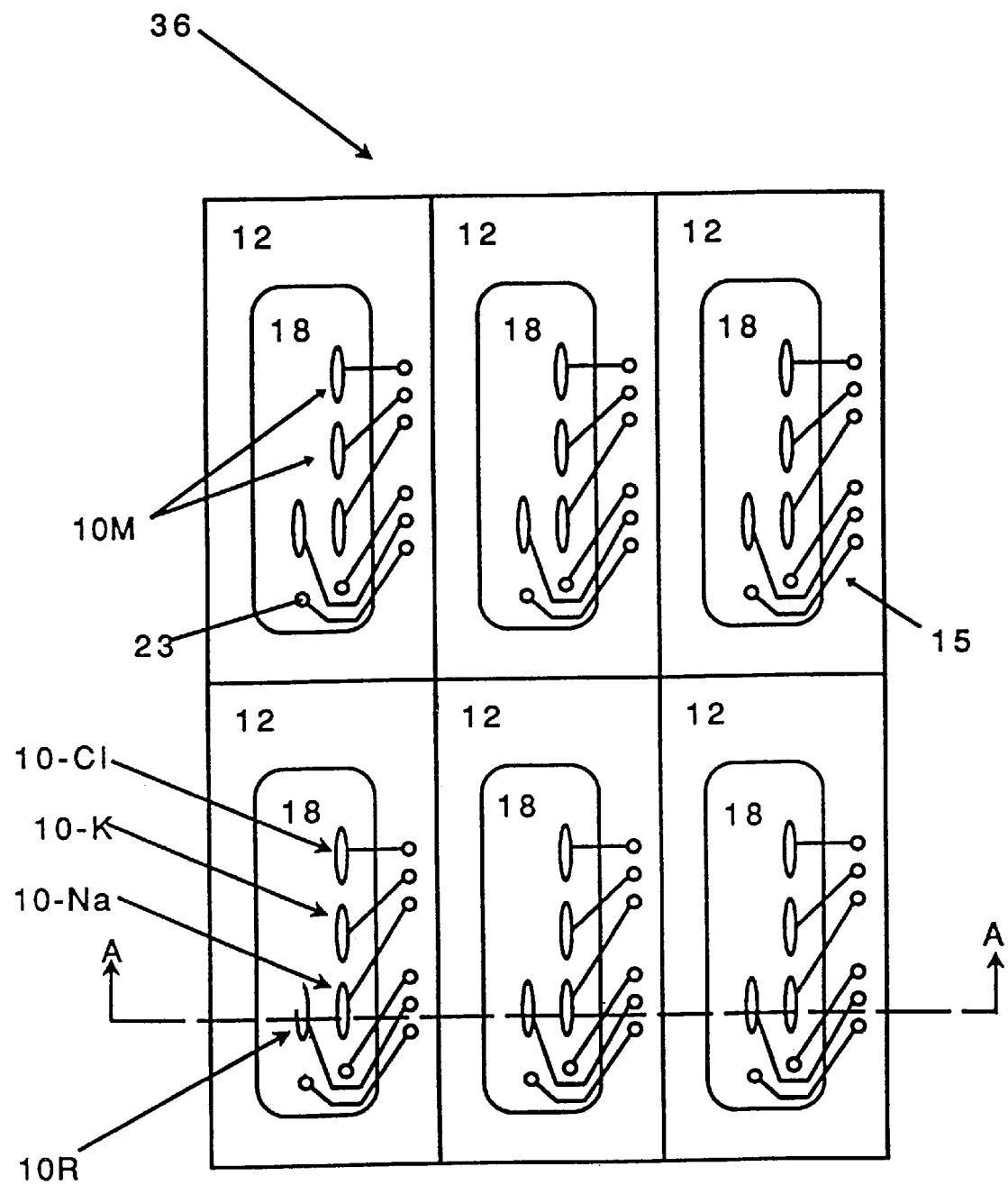
FIG. 2 is a plan view of a sensor base showing how various ISE sensors may be arrayed for testing; and, FIG. 3 is a sectional view taken along line A—A of FIG. 2 of a sodium ISE sensor incorporating the present invention.

FIG. 2 shows a substrate 36 comprising a number of individual sensor bases 12 arrayed in a regular pattern, the bases 12 being defined by scribing a regular pattern onto a contiguously formed single manufacturing piece suitable for handling by automated production equipment. After manufacturing processes are completed, the sensor bases 12 may be separated into a number of individual sensors 10. Each of the sensor bases 12 has integrated thereon in planar arrangement an array of ISE sensors 10 comprising a plurality of conductive paths 15 deposited in patterns terminating in electrical contacting pads 23, sensors 10 being comprised of individual layers 14, 16, and 18 (best seen in FIGS. 1a and 1b). The sensors 10 are designed to perform either reference or analyte measuring tasks and are preferably disposed in banks or rows with the sensor elements 10 being a reference function sensor 10R being on one side or row and the sensor elements 10 being a detecting or measuring function sensors 10-Na, 10-K, and 10-Cl on the other side or row. Each of the sensors 10 is individually connected by electrically conductive paths 15 which extend beyond the dielectric layer 14 to respective electrical contacts 23 which are formed on the top of the substrate 12. These contacts are located outside of the region that will be occupied by a flow channel member 31 which forms channels 34 over the respective sensor membranes 16 (see FIG. 3). The contacts 23 are positioned so that they may be contacted by appropriate electrical connectors. The electrical connectors 15 are connected using contacts 23 to electronic circuitry within a chemical analyzer (not shown) which provides the as needed multiplexer and electrometer amplifiers to selectively connect the various pairs of sensors 10R and 10M so as to facilitate the various measurements necessary for the operation of the sensor.

FIG. 3 shows a pair of channels 32R and 32M that are separate from one another at a fluid inlet section but are joined together at a fluid egress end of each groove, thereby defining fluid flow channels 34R and 34M through which reference fluid used in a calibration procedure and sample fluid to be tested are able to flow through. The flow channel member 31 is formed of a material which is chosen to be chemically inert with respect to solutions likely to be used in the sensor cartridge. The upper surface of the sensor membrane layer 16 is thusly in fluid and electrolytic contact with reference fluids and sample fluids supplied through the fluid flow channels 34R and 34M, respectively. Elastomer materials such as butyl rubber, halobutyl rubber, bromobutyl rubber, silicone, polyurethane or polyvinyl chloride with room temperatures mechanical properties of hardness in the range of 40 Shore A (ASTM D-2140) to 60 Shore A and a segment modulus at 10% strain in the range 0.7 to 4.2 MPa are preferred.

The amount of analyte in a sample liquid may be determined by using the sensor devices in pairs, with one sensor device being exposed to a reference or control fluid containing a known amount of analyte, and the other being exposed to a sample fluid containing an unknown amount of analyte. U.S. Pat. No. 5,284,568, assigned to the assignee of the present invention, is illustrative of such a device. Using well known calibration techniques, an assay may be performed in a comparative or differential method of measurement to determine the levels of an analyte in sample fluids.

Operation of the sensor 10 consists of a two point calibration procedure and then multiple test fluid analytical measurement steps. Both the two point calibration procedure and the sample measurements are comprised of two analytical determinations. The first calibration procedure step is accomplished by pumping a reference fluid into the reference flow channel 34R and then pumping the same reference fluid into the measuring flow channel 34M. Reference fluids are solutions with known ionic concentrations over the range to be measured. A potential is then measured by the electronics contained within the analyzer. The second calibration procedure step is accomplished by pumping a different reference fluid into the flow channel 34R. A potential is again measured by the analyzer. The response or slope of the sensor is calculated from the measured potentials and the known ionic concentrations of the reference fluids.

The first sample fluid measurement step consists of pumping a reference fluid into the flow channel 34M and then drawing the same reference fluid into the measuring flow channel 34R. A potentiometric signal is then measured by the electronics. The second sample fluid measurement step consists of pumping the sample fluid into the flow channel 34M. A potentiometric signal is measured again by the electronics. The concentration of the ion in the sample is calculated from the measured potentials and the known slope of the sensor and ionic concentration of the reference fluid.

As used in this specification, the term "fluid" includes liquids as well as gases, although at the present time liquids are primarily used. Also, although several reference sensor elements are shown, a single element can be used. The sensor elements may be along a curved path if desired.

The following examples are presented to illustrate the practice of this invention.

EXAMPLE 1

Membrane Paste Compositions Not Containing Water

This is an example illustrating the uselife of sodium, potassium and chloride ISE sensors like those described in U.S. Pat. No. 5,522,978 noted hereinabove. The pastes used to prepare the ion selective membranes were made by mixing the ingredients listed in Table 1 and without the deliberate incorporation of water into the membrane paste.

TABLE 1

| | Paste Weight Compositions | | |
|---|---|---|---|
| Ingredient | Sodium | Potassium | Chloride |
| Fluka Na III | 0.9% | N/A | N/A |
| Valinomycin | N/A | 0.9% | N/A |
| cPVC* | 8.4% | 8.4% | 8.6% |
| Dioctyl adipate | 17.0% | 17.0% | N/A |
| SiO$_2$ | 5.1% | 5.1% | 11.3% |
| Silane** | 3.0% | 3.0% | 2.9% |
| Dichloromethane | 3.9% | 3.9% | N/A |
| Isophorone | 61.6% | 61.6% | 62.1% |
| TDMAC*** | N/A | N/A | 15.0% |
| Borate**** | N/A | 0.050% | N/A |

*carboxylated polyvinyl chloride
**glycidoxypropyltrimethoxysilane
***tridodecylmethylammonium chloride
****Potassium tetra(chlorophenyl)borate The uselife of sodium sensors prepared according to the methods described hereinbefore and using a membrane prepared with paste constituents according to Table 1 was less than 24 hours, compared to a desired uselife of at least 48 hours. Uselife was determined as the number of hours a sensor could be exposed to a standard test fluid comprising a standard aqueous solution of sodium and potassium chloride and carbonate having a pH in the range about 9.0 to 9.5 and an ionic strength of approximately 150 millimolar without causing the calibration slope after exposure to deviate from the calibration slope before exposure by more than 10%.

EXAMPLE 2

Membrane Paste Compositions Containing Water

This is a comparative example illustrating the extended uselife of a sodium ISE sensor exemplary of this invention compared to the uselife of the state of the art ISE sensor of Example 1. The pastes used to prepare ion selective membranes for sodium, potassium and chloride including the incorporation of between about 0.50 percent by weight and 1.00 percent by weight of water were made by mixing the ingredients listed in Table 2 below:

TABLE 2

| | Paste Weight Compositions | | |
|---|---|---|---|
| Ingredient | Sodium | Potassium | Chloride |
| Fluka Na III | 0.9% | N/A | N/A |
| Valinomycin | N/A | 0.9% | N/A |
| Water | 0.75% | 0.75% | 0.75% |
| cPVC* | 8.4% | 8.4% | 8.6% |
| Dioctyl adipate | 17.0% | 17.0% | N/A |
| SiO$_2$ | 5.1% | 5.1% | 11.3% |
| Silane** | 3.0% | 3.0% | 2.9% |
| Dichloromethane | 3.9% | 3.9% | N/A |
| Isophorone | 61.6% | 61.6% | 62.1% |
| TDMAC*** | N/A | N/A | 15.0% |
| Borate**** | N/A | 0.050% | N/A |

*carboxylated polyvinyl chloride
**glycidoxypropyltrimethoxysilane
***tridodecylmethylammonium chloride
****Potassium tetra(chlorophenyl)borate The uselife of all three sensors prepared according to the methods described hereinbefore and using a membrane prepared with paste constituents according to Table 2 was greater than about 48 hours and as large as 72 hours in some instances and were therefore judged much more suitable for actual use compared to sensors made without water incorporated into the membrane paste.

Uselife of Sensors With Membranes Made According to Examples 1 and 2

The performance of the completed sensors 10 having membranes comprising the ingredients listed in Tables 1 and 2 was measured using standard operating protocols on a Dimension® AR Clinical Chemical System obtained from Dade Chemistry Systems Inc. (Newark, Delaware) equipped with appropriate pumps, calibrates, Multiply® ISE cartridges, electronics and operating software. The sensors were calibrated as described above with two levels of each electrolyte, and then a panel of test fluids consisting of two levels of aqueous buffered electrolytes, and three test fluids of serum based control products was analyzed. The calibrators or reference fluids were obtained from Dade Chemistry Systems Inc., and the sample fluids were Ciba-Corning Co.'s (Medfield, Me.) commercial Multiqual® controls. The reference fluids had multilevel concentrations of sodium ions, respectively MQ1, MQ2, and MQ3. The reference fluids concentrations were determined by gravimetric determination of the quantities of pure sodium, potassium and chloride salts. The control product concentration assignments were determined using multiple sensors made without water. The baseline results were obtained with new sensors, early in their life cycle so that the results for all cartridges were relative to unused new sensors.

The uselife of the sensors was determined by repeating the calibration procedure for groups of between 5 and 10 individual sensors during a period of 72 hours. After initial calibration determinations, the cartridges were left in a standby mode for 24 hours during which period a standard aqueous solution was slowly pumped through measuring flow channel 34M. The cartridges were subsequently re-tested to determined the calibration slope after 24 hours of simulated uselife. After 48 additional hours, for a total elapsed time of 72 hours, the calibration/testing cycle was repeated to determined the calibration slope after 72 hours of simulated uselife. Then a comparison was made between the calibration slopes of the sensors exposed to calibration and standard solutions for 72 hours and a control group of sensors that were exposed only to calibration solutions during initial calibration determinations. The results of uselife testing for the sodium sensor produced with and without water in the membrane paste composition are shown below in Table 3. Table 3 shows the MQ3 results for the sodium membrane which best demonstrated the improvement in performance obtained by the addition of water to the membrane paste.

TABLE 3

| | Example 1 | | | Example 2 | |
| --- | --- | --- | --- | --- | --- |
| Unit | Na Slope | Na Concentration Found | Unit | Na Slope | Na Concentration Found |
| 1 | 56.7 | 174.9 | 1 | 57.2 | 175.1 |
| 2 | 52.1 | 179.6 | 2 | 57.6 | 173.8 |
| 3 | 55.8 | 176.7 | 3 | 55.1 | 176.2 |
| 4 | 44.1 | 194.5 | 4 | 50.2 | 181.2 |
| 5 | 56.7 | 177.6 | 5 | 56.3 | 175.1 |
| 6 | 46.6 | 185.3 | 6 | 56.1 | 174.6 |
| Average | 52.0 | 181.4 | Average | 55.4 | 176.0 |

The reliability performance of the sodium sensors using membranes made from water-free paste was unsatisfactory. The degraded performance is related to a loss of selectivity for sodium. The average calibration slope was >55 mV/decade when 0.75% water was added to the paste, compared to a typical response of <53 mV/decade when no water was added. The well-known Nernst equation would yield a theoretical slope of about 59 mV/decade at the ambient temperature these test were made. On this comparative basis, it was judged that sodium membranes made using pastes incorporating water provided a statistically significant increase in uselife.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A ion-selective-electrode membrane paste for producing a membrane for determining the presence of sodium in fluids, the membrane paste comprising:

a polymeric matrix;

water between about 0.50 percent and 1.00 percent by weight;

an ionophore selective for sodium; and, a silane coupling agent mixed uniformly within the paste, said coupling agent comprising glycidoxypropyltrimethoxysilane.

2. The membrane paste according to claim 1 wherein the polymeric matrix is selected from the group consisting of poly(vinyl chloride), carboxylated poly(vinyl chloride), poly (styrene-co-styrene sulfonic add), poly(vinyl chloride-co-styrene sulfonic acid), poly(vinyl chloride-co-styrene carboxylic acid) and mixtures thereof.

3. The membrane sensor utilizing a paste according to claim 1 wherein the ionophore selective for sodium is selected from the group consisting of naturally occurring monensin, monensin ester derivatives including methyl, ethyl, butyl, and dodecyl ester monensins, polyether diamide, biscrown ether, cryptand, calixarene, hemispherand, 16-crown-5 derivatives, and (4-octadecanoylocymethyl)-N,N,N',N'-tetracylcohexyl-1,2-phenylenedioxydiacetamide.

4. The membrane paste according to claim 1 further comprising a solvent selected from the group consisting of phthalates, sebacates, aromatic and aliphatic ethers, phosphates, mixed aromatic aliphatic phosphonates, adipates, nitrated ethers or esters, 2-ethyl hexyl adipate and dioctyl sebacate or mixtures thereof.

\* \* \* \* \*